United States Patent [19]

Heitzman

[11] Patent Number: 4,574,798
[45] Date of Patent: Mar. 11, 1986

[54] SURGICAL APPLIANCE SUPPORT

[76] Inventor: William G. Heitzman, 1853 Melville Cir., Brunswick, Ohio 44212

[21] Appl. No.: 560,336

[22] Filed: Dec. 12, 1983

[51] Int. Cl.⁴ .......................................... A61M 16/00
[52] U.S. Cl. ........................ 128/205.22; 128/207.14; 128/DIG. 26
[58] Field of Search ...................... 128/202.12, 204.18, 128/205.22, 207.14, 207.16, 207.17, 207.18, DIG. 26; 604/174, 176, 178, 179, 180

[56] References Cited

U.S. PATENT DOCUMENTS

| 804,272 | 11/1905 | Schwarz | 128/207.18 |
|---|---|---|---|
| 2,280,915 | 4/1942 | Johnson | 604/179 |
| 3,302,643 | 2/1967 | Allmand | 128/205.22 |
| 3,461,877 | 8/1969 | Morch | 128/207.14 |
| 3,491,752 | 1/1970 | Cowley | 128/205.22 |
| 3,677,250 | 7/1982 | Thomas | 604/180 |
| 4,029,103 | 6/1977 | McConnell | 604/179 |
| 4,056,098 | 11/1977 | Michel et al. | 128/205.13 |
| 4,164,943 | 8/1979 | Hill et al. | 128/DIG. 26 |
| 4,430,995 | 2/1984 | Hilton | 128/205.12 |
| 4,438,763 | 3/1984 | Zablen | 604/179 |

Primary Examiner—Henry J. Recla
Attorney, Agent, or Firm—Baldwin, Egan & Fetzer

[57] ABSTRACT

A surgical appliance support is provided which is secured to the patient's chest or back and accommodates respiration tubes, oxygen-air mixing elements, catheter suctioning lung equipment, alarm devices, and the like. The support is comfortable, sanitary, and safe for use with long-term patients.

5 Claims, 6 Drawing Figures

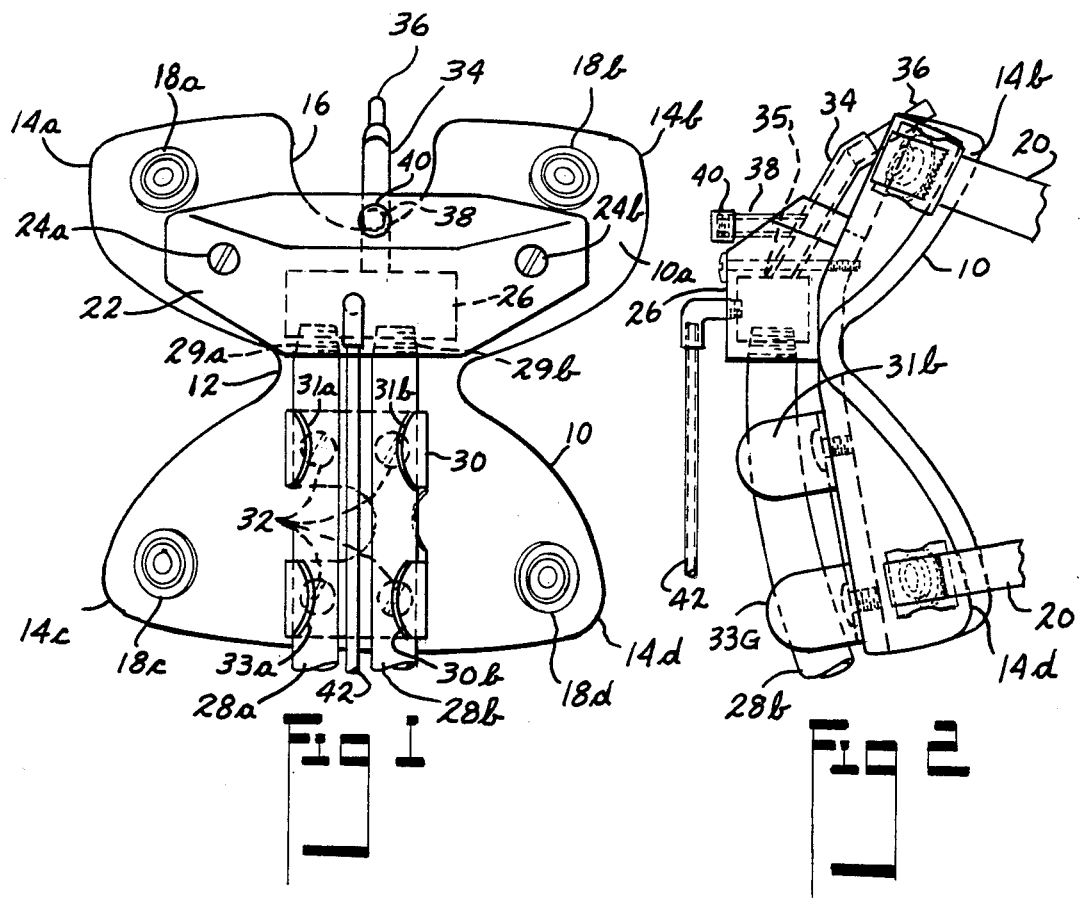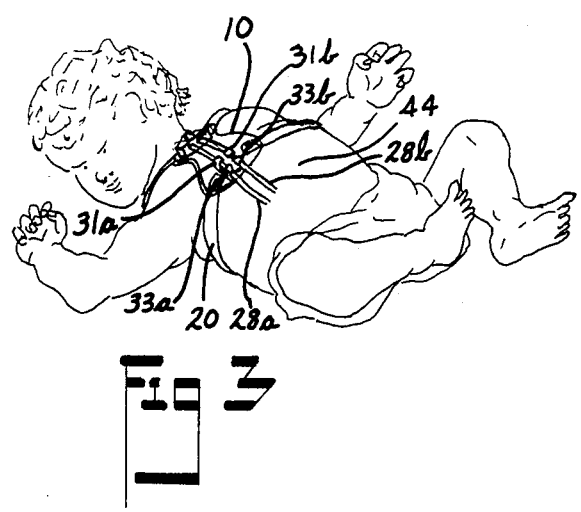

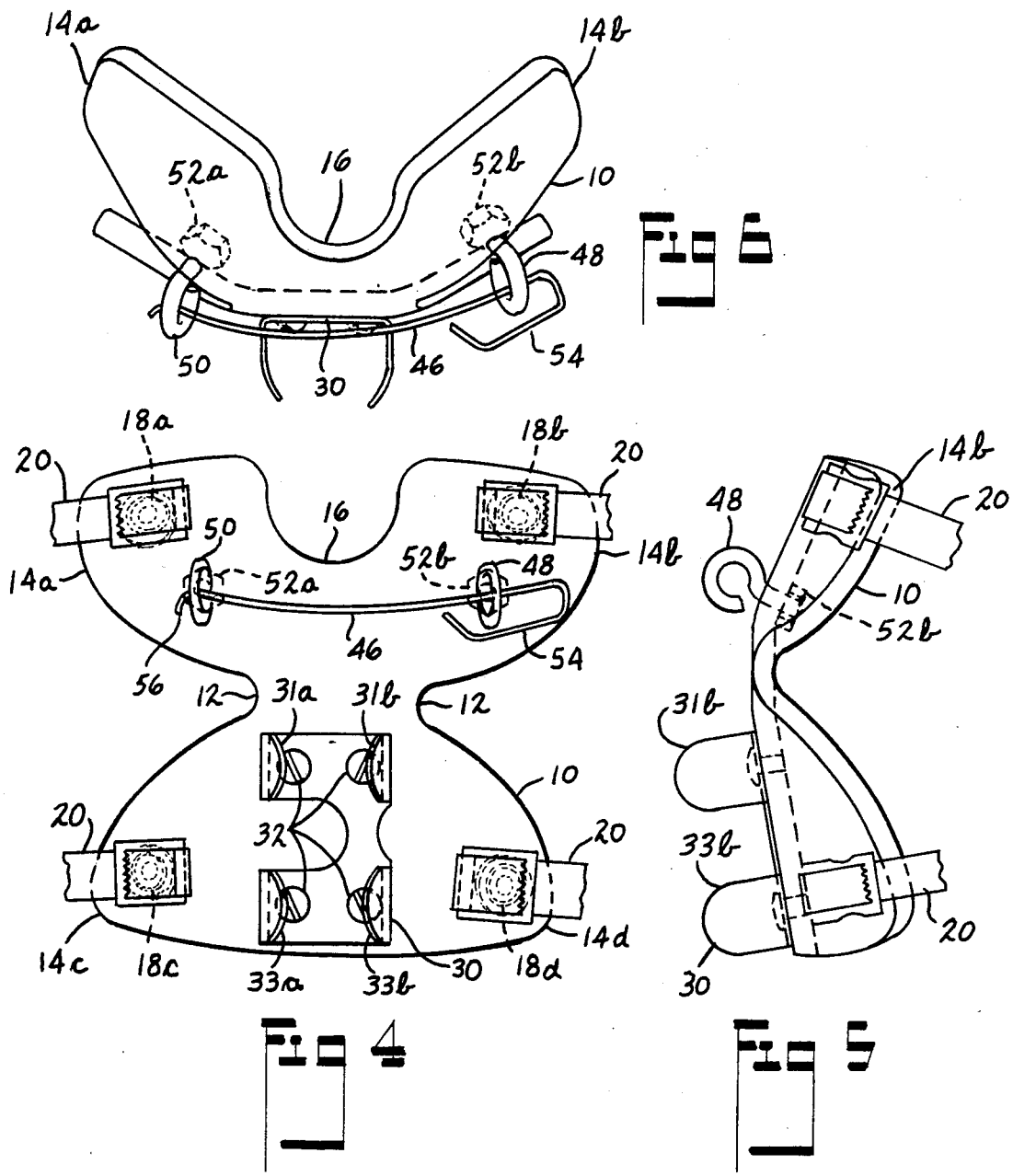

SURGICAL APPLIANCE SUPPORT

This invention relates to a new and novel surgical appliance support and more particularly to a respiratory adapter block support and tube support for use primarily with intubated tracheostomy and tracheotomy patients, and which support is operable to hold respirator tubes in a stationary position on the chest or back of the patient thereby decreasing irritation caused by tube movement, to position an oxygen-air mixing chamber on the patient's chest or back thereby increasing neck mobility, to provide a larger air-oxygen mixing chamber to facilitate diffusion of gases in and out of the patient, to accommodate a suction catheter thereby allowing deep suctioning of the lungs without disconnecting the patient from the respirator, to accommodate pressure sensors with associated alarm systems thereby monitoring patient respiration, and to allow the patient the comfort of lying on his back or stomach by relocating the modified appliance from his chest to his back.

BACKGROUND OF THE INVENTION

The mouth, throat or tracheal passage in certain medical patients may be blocked by blood, mucus or other material. In acute situations, it may be necessary to solve this problem by making an incision in the trachea of the patient and inserting a tube to allow for the free passage of air or oxygen. Frequently breathing is augmented and respiration is monitored. This equipment must be maintained in proper position on the patient for extended periods of time. Traditionally, the tubes, hoses and leads associated with such equipment are held to the neck of the patient by means of tape adhering to the skin. This method entails several disadvantages. Sweat, blood, saliva or other body secretions will wet the tape causing it to loosen, thus allowing the tubes, hoses and leads to be dislodged. Spasms or normal movements of the patient may cause life-saving equipment to be displaced. Chafing, tearing and trauma to tissue often result. Sanitation is a continuous problem. Also, repeated application and removal of adhesive tape causes discomfort to the patient.

Heretofore, several types of support devices have been utilized to provide for the support of tubes and like devices for use in patient care such as those illustrated in U.S. Pat. No. 4,282,871 to Chodorow et al. and U.S. Pat. No. 4,191,180 to Colley et al. which disclose support devices for nasal tubes. U.S. Pat. No. 4,331,143 to Foster, U.S. Pat. No. 4,223,671 to Muto and U.S. Pat. No. 3,946,742 to Eross disclose support devices for endotracheal tubes fitted to the mouth. U.S. Pat. No. 4,290,425 to Helfer et al.; U.S. Pat. No. 4,261,349 to Lambson et al.; U.S. Pat. No. 3,722,508 to Roberts; U.S. Pat. No. 3,055,365 to Tezak; and U.S. Pat. No. 2,586,940 to Green disclose medical support devices.

SUMMARY OF THE INVENTION

The surgical appliance support disclosed herein provides a medical appliance for use primarily with tracheostomy and tracheotomy patients. The appliance includes a support member contoured to fit across the patient's chest or back. Anchored to the support member are snaps to which straps may be detachably secured, thus enabling the support member to be tied around the patient's torso. In one embodiment, a bracket and a wire fastener anchored to the support member provide means whereby respiratory tubes may be removably secured to the support member. In another embodiment, respiration tubes may be connected to an enlarged mixing block which is anchored to the support member. The mixing block is provided with a mixing chamber in which oxygen and air are mixed together, as required, to meet the patient's needs. An alarm indicator tube, which senses gas pressure and warns of possible respiration difficulties of the patient, may also be attached to the mixing block. A distribution tube connected to the mixing block allows continuous movement of gases through the mixing block to and from the patient. The distribution tube is fitted with a capped suction catheter opening to permit deep suctioning of the patient without disconnecting the patient from the system. The support member, with mixing block, may be placed on the patient's back. Flexible corrugated tubing runs up the back and around the front of the neck where it connects to the tracheostomy or tracheotomy tube. This arrangement resembles a person wearing a scuba diving air tank, with connecting air supply tubes.

It is an object of the invention to provide a surgical appliance support which detachably positions respiration equipment firmly and stably on a patient for extended periods of time thereby increasing patient safety and comfort.

A further object of the invention is to provide a surgical appliance support which will detachably hold respiratory tubes in a stationary position on the chest or back of the patient thereby increasing patient safety and comfort.

Another object of this invention is to provide a surgical appliance support which detachably positions the oxygen-air mixing chamber on the patient's upper chest or back (instead of under the chin), thereby giving the patient more neck mobility and thus giving the physician more access to the trachea.

Another object of this invention is to provide a surgical appliance support which accommodates an enlarged oxygen-air mixing chamber, thereby facilitating the flow of gas through the respiration system and allowing diffusion of gases in and out of the patient with less exertion.

Another object of this invention is to provide a surgical appliance support which accommodates a capped suction catheter opening thereby allowing deep suctioning of the lungs without disconnecting the patient from the respirator.

A further object of the invention is to provide a surgical appliance support that is unusually sanitary and which may be discarded after use or sterilized and reused.

Another object of the invention is to provide an appliance support which allows the patient to lie on his back or stomach by use of a modified support member placed on either the patient's chest or back.

These and other objects, advantages, characteristics and features of this invention will be apparent from the following description taken in conjunction with the accompanying drawings, wherein:

BRIEF DESCRIPTION OF THE DRAWINGS

FIG. 1 is a front elevational view of the surgical appliance support of the invention fitted with respirator tubes, an oxygen-air mixing chamber, an alarm indicator tube, and a gas distribution tube fitted with a capped suction catheter opening;

FIG. 2 is a side elevational view of the surgical appliance support shown in FIG. 1;

FIG. 3 is a perspective view of the surgical appliance support of FIG. 1 shown attached to an infant patient;

FIG. 4 is a front elevational view of the surgical appliance support of the invention and shown with a tube support bracket and a tube retainer thereon;

FIG. 5 is a side elevational view of the surgical appliance support shown in FIG. 4; and FIG. 6 is a top plan view of the surgical appliance support shown in FIG. 4.

DESCRIPTION OF PREFERRED EMBODIMENTS

Referring first to FIGS. 3, 4, 5 and 6, there are illustrated views of the surgical appliance support 10, constructed in accordance with the invention, and preferably formed of thermoplastic or other like material chosen for easy care and long life. The support or base or holder 10 is preferably contoured to conform to the patient's chest or corresponding back portion and can be made to fit any size patient. The term chest has the same definition as found in *Webster's New Twentieth Century Dictionary*, i.e. the thorax, the part of the body enclosed by the ribs and breastbone. The support 10 is of a generally butterfly configuration having a narrowed waist portion 12, widened ear portions 14a, 14b, 14c and 14d, (which stabilize the device on the patient) and a recess 16. The narrowed waist portion 12 serves to reduce the weight of the support 10 and increase patient comfort, while the widened ear portions 14a, 14b, 14c, 14d serve as anchorage points for snaps 18a, 18b, 18c, 18d or other like fasteners. Snaps 18a, 18b, 18c, 18d are used to secure a suitable securing means such as the adjustable harness 20 that fits around the chest or back or back of the neck of the patient to hold the holder 10 in place thereon.

In the embodiment illustrated in FIGS. 1 and 2, the holder 10 is provided with a gas or air-oxygen mixing chamber element 22 that is mounted with screws 24a, 24b, or other suitable fasteners to surface 10a of the holder 10. The mixing chamber element 22 (configured to fit on the support 10) is preferably constructed of metal, can be sterilized and includes a gas-tight mixing chamber 26 thereon. The mixing chamber 26 is used to mix the correct amounts of air and oxygen according to the patient's needs, and is preferably larger than those conventionally available and in use, thereby facilitating diffusion of gases in and out of the patient with less exertion than heretofore. Respirator tubes 28a, 28b, supply air or oxygen to the mixing chamber 26 through gas-tight port connections 29a, 29b, and allow for the removal of gases respired by the patient into the mixing chamber 26. A bracket 30 secured by screws 32 or other suitable fasteners removably holds the respirator tubes 28a, 28b to the holder 10. More specifically, the bracket 30 has an upper pair of oppositely spaced partially flexible tabs 31a, 31b, and a lower pair of oppositely spaced tabs 33a, 33b, such tabs contoured and positioned to detachably support the pair of flexible tubes 28a, 28b, therebetween as best shown in FIGS. 1 and 3. A gas distribution tube 34 is attached to the mixing chamber 26 through a gas-tight connection 35. Removably fitted to the gas distribution tube 34 is a tracheal tube 36 which conveys gases to and from the mixing chamber 26 through the gas distribution tube 34, to and from the patient. The removably fitted tracheal tube 36 may be replaced, cleaned or substituted in size according to patient needs. The gas distribution tube 34 and the tracheal tube 36 are angled (FIG. 2) to pass through the recess 16 of the holder 10, thereby enabling the conveying of gases to and from the trachea of the patient, while allowing access to and movement of the patient's neck. The gas distribution tube 34 preferably communicates with a suction catheter opening 38 and cap 40, which extends forwardly of the holder 10 for easy access by attending personnel. Under normal conditions, the cap 40 seals the suction catheter opening 38 maintaining the gas-tight integrity of the gas distribution tube 34 and mixing chamber 26, but when medical conditions warrant, the cap 40 may be removed and the patient's lungs deep suctioned without disconnecting the patient from the respiration shown) may be connected to the mixing chamber 26, via the system. A conventional associated pressure alarm system (not shown) may be connected to the mixing chamber 26, via the sensor tube 42 serving to provide a warning of equipment malfunction or cessation of patient breathing.

FIG. 3 illustrates the holder 10 attached to the chest of an infant patient 44 and also shows the connection of associated respiration equipment thereto.

FIGS. 4, 5 and 6 illustrate a modification of the basic surgical appliance support holder 10 wherein there is incorporated a detachable tube retainer in the form of a wire fastener 46 that serves to removably hold respirator tubes in coaction with the tabs 31a, 31b, 33a, 33b. The elongated wire fastener 46 is preferably held by two eyelets 48 and 50, such eyelets being preferably fastened to upper ear portions 14b, 14a, respectively of the holder 10 by nuts 52b, 52a, respectively. The wire fastener 46 preferably has a loop portion 54 which is held by eyelet 48. The wire fastener 46 preferably has a distal end 56 which is held by partially open eyelet 50, but which may be quickly and easily disengaged therefrom. This embodiment has utility where respiration tubes must be held stationary against a patient for long periods of time but where the patient's condition does not call for deep suctioning of lungs.

Thus, the invention provides a tube and surgical appliance support 10 contoured to fit a patient's chest, and securing means 20 for detachably securing support 10 to the patient's chest as shown in FIG. 3.

More specifically, the invention provides a chest mounted tube and surgical appliance support 10 for use with tracheostomy and tracheotomy patients, for example, including, a base 10 contoured to fit a patient's chest, a tube support bracket 30 secured to such base, a detachable tube retainer 46 spaced from and upwardly of the bracket 30 for detachably retaining tubes 28a, 28b, thereat on the base, and securing means 20 for detachably securing the base 10 to a patient's chest. The tube support bracket 30 includes at least one pair of opposite spaced tabs 31a, 31b, for example, contoured and positioned to detachably support the pair of flexible tubes 28a, 28b therebetween. The tube retainer 36 includes a pair of spaced eyelets 48, 50 secured to the base 10, and the elongated wire fastener 46 hinged to one eyelet 48 and having its free distal end 56 formed into a hook portion that is detachably positioned in the other eyelet 50 to detachably retain tubes on the base between the wire fastener and the base. The base 10 has a generally hourglass configuration including upper spaced ear portions 14a, 14b, lower spaced ear portions 14c, 14d, and a narrowed waist portion 12 all contoured to fit a patient's chest. Also included is a gas mixing chamber 26 secured to the base 10 for mixing predetermined amounts of air and oxygen, such chamber 26 including air supply and respiratory tubes 28a, 28b secured to such bracket 30 and tube retainer 46. Also, the invention broadly contemplates a tube and surgical appliance support 10 contoured to fit a patient's chest, securing means 20 for detachably securing said support to the patient's chest, and securement means 30, 46 on said support for detachably securing surgical applicances thereto.

The terms and expressions which have been used are used as terms of description and not of limitation, and there is no intention in the use of such terms and expressions of excluding any equivalents of any features shown, or described, or portions thereof, and it is recognized that various modifications are possible within the scope of the invention claimed.

What is claimed is:

1. An appliance for use on a tracheotomy patient comprising a plate-like base comprising means contoured to lie upon a patient's chest or corresponding back portion, means for stably supporting said base on said chest or back portion, tube means for supplying preselected gas or gases, tube support means on said base removably retaining said tube means on said base, chamber means mounted on said base connector to said tube means effective to receive said preselected gas or gases therein from said tube means, trachea tube means adapted to be inserted into the trachea of a patient connected to said chamber means for directing the gas or gases in said chamber to the trachea of the patient.

2. An appliance as defined in claim 1 and further wherein the first mentioned tube means comprises a pair of tubes separately connectable to the chamber means and adapted to be separately connected to sources of air and oxygen for providing air and oxygen to said chamber means.

3. An appliances as defined in claim 1 and further comprising means for detachably securing the base to the patient.

4. An appliance as defined in claim 1 and further comprising securement means for detachably securing surgical appliances to said base.

5. An appliance as defined in claim 4 and further wherein the securement means comprises a pair of spaced eyelets secured to the base, and an elongated wire fastener hinged to one eyelet and having its free distal end formed into a hook portion that is detachably positioned in the other eyelet to detachably retain the tube means on the base.

* * * * *